(12) United States Patent
Mou et al.

(10) Patent No.: US 8,425,477 B2
(45) Date of Patent: *Apr. 23, 2013

(54) METHOD AND SYSTEM FOR PROVIDING TARGETED AND INDIVIDUALIZED DELIVERY OF COSMETIC ACTIVES

(75) Inventors: Tsung-wei Robert Mou, Stony Brook, NY (US); Fatemeh Mohammadi, Hauppauge, NY (US); Lisa Qu, Flushing, NY (US); Anna Czarnota, Huntington Station, NY (US); Tamar Lara Kamen, New York, NY (US)

(73) Assignee: ELC Management LLC, New York, NY (US)

( * ) Notice: Subject to any disclaimer, the term of this patent is extended or adjusted under 35 U.S.C. 154(b) by 556 days.

This patent is subject to a terminal disclaimer.

(21) Appl. No.: 12/533,107

(22) Filed: Jul. 31, 2009

(65) Prior Publication Data

US 2010/0068247 A1   Mar. 18, 2010

Related U.S. Application Data

(60) Provisional application No. 61/097,273, filed on Sep. 16, 2008.

(51) Int. Cl.
 *H04N 5/225* (2006.01)
 *A61K 9/70* (2006.01)

(52) U.S. Cl.
 USPC ........... 604/304; 424/443; 424/447; 424/449; 348/86

(58) Field of Classification Search .................. 604/304; 424/443, 447, 449; 347/86
 See application file for complete search history.

(56) References Cited

U.S. PATENT DOCUMENTS

| | | | |
|---|---|---|---|
| 3,154,070 A | 10/1964 | Meckelburg | |
| 3,499,446 A | 3/1970 | Tsuneizumi et al. | |
| 5,016,173 A | 5/1991 | Kenet et al. | |
| 5,538,732 A | 7/1996 | Smith et al. | |
| 5,622,692 A | 4/1997 | Rigg et al. | |
| 5,958,560 A | 9/1999 | Ewan | |
| 6,001,380 A | 12/1999 | Smith et al. | |
| 6,293,284 B1 | 9/2001 | Rigg | |
| 6,502,583 B1 | 1/2003 | Utsugi | |
| 6,516,245 B1 | 2/2003 | Dirksing et al. | |
| 6,530,379 B2 | 3/2003 | Iosilevich | |
| 6,571,003 B1 | 5/2003 | Hillebrand et al. | |
| 6,574,801 B1 | 6/2003 | Harens et al. | |
| RE38,246 E | 9/2003 | Leonard et al. | |
| 6,761,697 B2 | 7/2004 | Rubinstenn et al. | |
| 6,770,286 B1 * | 8/2004 | Berry | 424/402 |
| 6,810,130 B1 | 10/2004 | Aubert et al. | |
| 6,856,861 B2 | 2/2005 | Dirksing et al. | |
| 6,937,755 B2 | 8/2005 | Orpaz et al. | |
| 6,959,119 B2 | 10/2005 | Hawkins et al. | |
| 7,006,657 B2 | 2/2006 | Bazin | |
| 7,079,158 B2 | 7/2006 | Lambertsen | |
| 7,165,559 B1 | 1/2007 | Goodman | |
| 7,324,668 B2 | 1/2008 | Rubinstenn et al. | |
| 7,387,787 B2 | 6/2008 | Fox | |
| 7,424,139 B1 | 9/2008 | Stefan et al. | |
| 7,437,344 B2 | 10/2008 | Peyrelevade | |
| 7,634,103 B2 | 12/2009 | Rubinstenn et al. | |
| 8,077,931 B1 | 12/2011 | Chatman et al. | |
| 2002/0090123 A1 | 7/2002 | Bazin | |
| 2003/0063794 A1 | 4/2003 | Rubinstenn et al. | |
| 2004/0022830 A1 | 2/2004 | Nakamura et al. | |
| 2004/0078278 A1 | 4/2004 | Dauga et al. | |
| 2004/0102750 A1 | 5/2004 | Jameson | |
| 2006/0104931 A1 | 5/2006 | Fukutome et al. | |
| 2006/0197775 A1 | 9/2006 | Neal | |
| 2007/0258656 A1 | 11/2007 | Aarabi | |
| 2008/0014231 A1 | 1/2008 | Okano | |
| 2008/0058915 A1 | 3/2008 | Chang | |
| 2008/0163344 A1 | 7/2008 | Yang | |
| 2009/0129631 A1 | 5/2009 | Faure et al. | |
| 2009/0133206 A1 | 5/2009 | Benjamin et al. | |

(Continued)

FOREIGN PATENT DOCUMENTS

DE   102005020938 A1 * 11/2006
EP   1433418 A1 * 6/2004

(Continued)

OTHER PUBLICATIONS

PCT International Search Report; International Application No. PCT/US2009/041618; Completion Date: Dec. 4, 2009; Date of Mailing: Dec. 4, 2009.
PCT Written Opinion of the International Searching Authority, or the Declaration; International Application No. PCT/US2009/041618; Completion Date: Dec. 4, 2009; Mailing Date: Dec. 4, 2009.
PCT International Search Report; International Application No. PCT/US2009/052525; Completion Date: Feb. 25, 2010; Date of Mailing: Mar. 2, 2010. (Related U.S. Appl. No. 12/533,107).
PCT Written Opinion of the International Searching Authority, or the Declaration; International Application No. PCT/US2009/052525; Completion Date: Feb. 25, 2010; Mailing Date: Mar. 2, 2010. (Related U.S. Appl. No. 12/533,107).

(Continued)

*Primary Examiner* — Gina C Justice
(74) *Attorney, Agent, or Firm* — Martin W. Haerter

(57) ABSTRACT

A system and method are provided for targeted and individualized delivery of multiple skin benefit agents to the skin of a user. The image of a predetermined treatment area of the user's skin is first captured by an imaging device. The captured image data is then analyzed by a computing device to generate a unique skin profile for the user, which is indicative of the skin conditions at the predetermined treatment area. Based on such skin profile, a printing device prints out one or more cosmetic delivery sheets that can be applied to the predetermined treatment area. Each of the cosmetic delivery sheets contains a substrate with multiple isolate, discrete regions, while at least two of the regions are imprinted with different skin benefit agents for treating different skin conditions of the predetermined treatment area according to the unique skin profile of the user.

6 Claims, 3 Drawing Sheets

U.S. PATENT DOCUMENTS

| | | |
|---|---|---|
| 2009/0231356 A1 | 9/2009 | Barnes et al. |
| 2009/0260648 A1 | 10/2009 | Castelluccio |
| 2010/0226531 A1 | 9/2010 | Goto |

FOREIGN PATENT DOCUMENTS

| | | |
|---|---|---|
| EP | 1 459 782 | 9/2004 |
| EP | 1813167 | 8/2007 |
| JP | 55-164623 | * 12/1980 |
| JP | 7-231883 | 9/1995 |
| JP | 08-308634 | 11/1996 |
| JP | 2001-346627 | 12/2001 |
| KR | 20-0416534 | 5/2006 |
| KR | 10-2008-0059157 | 6/2008 |
| TW | 200426655 | 12/2004 |
| WO | WO97/29441 | 8/1997 |
| WO | WO98/37811 | 9/1998 |
| WO | WO00/00059 | 1/2000 |
| WO | WO01/04840 | 1/2001 |
| WO | WO 02/01499 | 1/2002 |
| WO | WO2005/058114 | 6/2005 |
| WO | WO2007/006559 | 1/2007 |
| WO | WO 2007/021972 | 2/2007 |
| WO | WO2007/123380 | 11/2007 |
| WO | WO 2008/010167 | 1/2008 |
| WO | WO2009/137277 | 11/2009 |

OTHER PUBLICATIONS

PCT International Search Report; International Application No. PCT/US2011/036288; Completion Date: Jan. 31, 2012; Date of Mailing: Feb. 9, 2012.

PCT Written Opinion of the International Searching Authority; International Application No. PCT/US2011/036288; Completion Date: Jan. 31, 2012; Mailing Date: Feb. 9, 2012.

PCT International Search Report; International Application No. PCT/US2011/036292; Completion Date: Jan. 31, 2012; Date of Mailing: Feb. 9, 2012.

PCT Written Opinion of the International Searching Authority; International Application No. PCT/US2011/036292; Completion Date: Jan. 31, 2012; Mailing Date: Feb. 9, 2012.

Supplementary European Search Report; EP09814947; Completion Date: Oct. 10, 2011; Date of Mailing: Oct. 24, 2011.

* cited by examiner

METHOD AND SYSTEM FOR PROVIDING TARGETED AND INDIVIDUALIZED DELIVERY OF COSMETIC ACTIVES

CROSS-REFERENCE TO RELATED APPLICATIONS

This claims priority to U.S. Provisional Patent Application No. 61/097,273, filed Sep. 16, 2008.

FIELD OF THE INVENTION

The present invention relates to method and system for achieving targeted and individualized delivery of one or more skin benefit agents to the skin of an user in need of such skin benefit agents, and to devices in the form of a single-use sheet for containing and delivering the skin benefit agents to one or more targeted areas of the skin. In particular, the invention relates to a method of delivering one or more skin benefit agents to targeted areas of the facial skin of a user based on the unique skin profile of such user and to a cosmetic sheet mask which incorporates one or more cosmetic or dermatological preparations for application to and treatment of the targeted areas of the skin of the user.

BACKGROUND OF THE INVENTION

A variety of cosmetic patches or devices are commercially marketed or described as being useful for the delivery of skin care actives such as vitamins, anti-acne actives, moisturizers, and the like. It has been known to use cosmetic sheets comprised of various materials, such as non-woven cotton, elastically extendable or stretchable materials, thermoplastics, tacky gel, etc., impregnated with various cosmetic or dermatological preparations, for application to the skin of the face, the neck and other areas of the body. The cosmetic sheets comprise a flexible support adapted to conform to the target areas when applied. The sheets also contain a system for containing and delivering skin benefit agents to the skin to which the sheet is applied. Currently, however, facial sheet masks on the market are fully impregnated with active ingredients and are applied to the entire face so as to deliver these ingredients to the entire face. Alternatively, a patch is applied only to certain areas, such as, under the eyes, to deliver the skin benefit agent to only this locus. However, these articles suffer drawbacks resulting in undesirable in-use characteristics as perceived by the consumer. For example it has heretofore not been possible with known full facial masks to target one or more specific areas with one or more skin benefit agents, but only to treat the entire face with one composition. Most consumers have different concerns for their skin in different areas of their face. For example many consumers have combination skin in which the T-zone area (forehead, nose and chin) is oily while the remainder of the face is dry. For another example some consumers may have lines and wrinkles at the forehead, eye, and mouth areas, dry or flaky skin at the cheek areas, and hyperpigmentation spots at other areas. Each region would need different treatment products to address the different concerns. Conventional masks can only address one concern at a time by treating the entire facial skin, rather than only the targeted areas.

There is therefore a need by consumers for cosmetic sheets which can deliver multiple skin benefit agents to various targeted areas of the skin of a user to address different skin conditions of such a user based on his or her unique skin profile.

SUMMARY OF THE INVENTION

The cosmetic sheets according to the present invention are provided with discrete regions, which are imprinted with different skin benefit agents, so when such cosmetic sheets are applied to and conformed to the skin, they can accurately deliver pre-determined dosages of different skin care formulations to the skin for treating different skin conditions or providing different skin benefits. More preferably, the cosmetic sheets of the present invention are not mass-produced like the conventional "one-type-fits-all" products, but are specifically customized for individual users according to their unique skin profiles.

Accordingly, the present invention in one aspect relates to a system for targeted and individualized delivery of multiple skin benefit agents to the skin of a user. Such system includes at least: (a) an imaging device for capturing an image of a predetermined treatment area of the user's skin; (b) an analyzing device communicatively connected with the imaging device for receiving data representative of the captured image from the imaging device, analyzing such data, and generating a skin profile indicative of the conditions of the predetermined treatment area of the user's skin; and (c) a printing device communicatively connected with the analyzing device for printing one or more cosmetic delivery sheets, wherein the cosmetic delivery sheets are arranged and constructed for conforming to the predetermined treatment area of the user's skin, wherein each of the cosmetic delivery sheets comprises a substrate with multiple isolate, discrete regions, wherein at least two of the isolate, discrete regions are imprinted with different skin benefit agents for treating different skin conditions of the predetermined treatment area according to the skin profile generated by the analyzing device.

The present invention in another aspect relates to a cosmetic delivery sheet arranged and constructed for conforming to a predetermined treatment area of the skin of a user. Such a cosmetic delivery sheet includes at least a substrate with multiple isolate, discrete regions, wherein at least two of the isolate, discrete regions are imprinted with different skin benefit agents for treating different skin conditions of the predetermined treatment area.

The present invention in a further aspect relates to a printer that contains cartridges filled with compositions containing skin benefit agents. Preferably, but not necessarily, such a printer is constructed to print the skin benefit agents onto a substrate through a heatless printing process.

The present invention in yet another aspect relates to a method for targeted and individualized delivery of multiple skin benefit agents to the skin of a user, which includes at least: (a) capturing an image of a predetermined treatment area of the user's skin; (b) analyzing the captured image data; (c) generating a skin profile indicative of the conditions of the predetermined treatment area of the user's skin; and (d) printing one or more cosmetic delivery sheets based on the generated skin profile, wherein the cosmetic delivery sheets are arranged and constructed for conforming to the predetermined treatment area of the user's skin, wherein each of the cosmetic delivery sheets comprises a substrate with multiple isolate, discrete regions, wherein at least two of the isolate, discrete regions are imprinted with different skin benefit agents for treating different skin conditions of the predetermined treatment area.

Other aspects and objectives of the present invention will become more apparent from the ensuing description, examples, and claims.

DETAILED DESCRIPTION OF THE INVENTION AND PREFERRED EMBODIMENTS THEREOF

Figure 1:
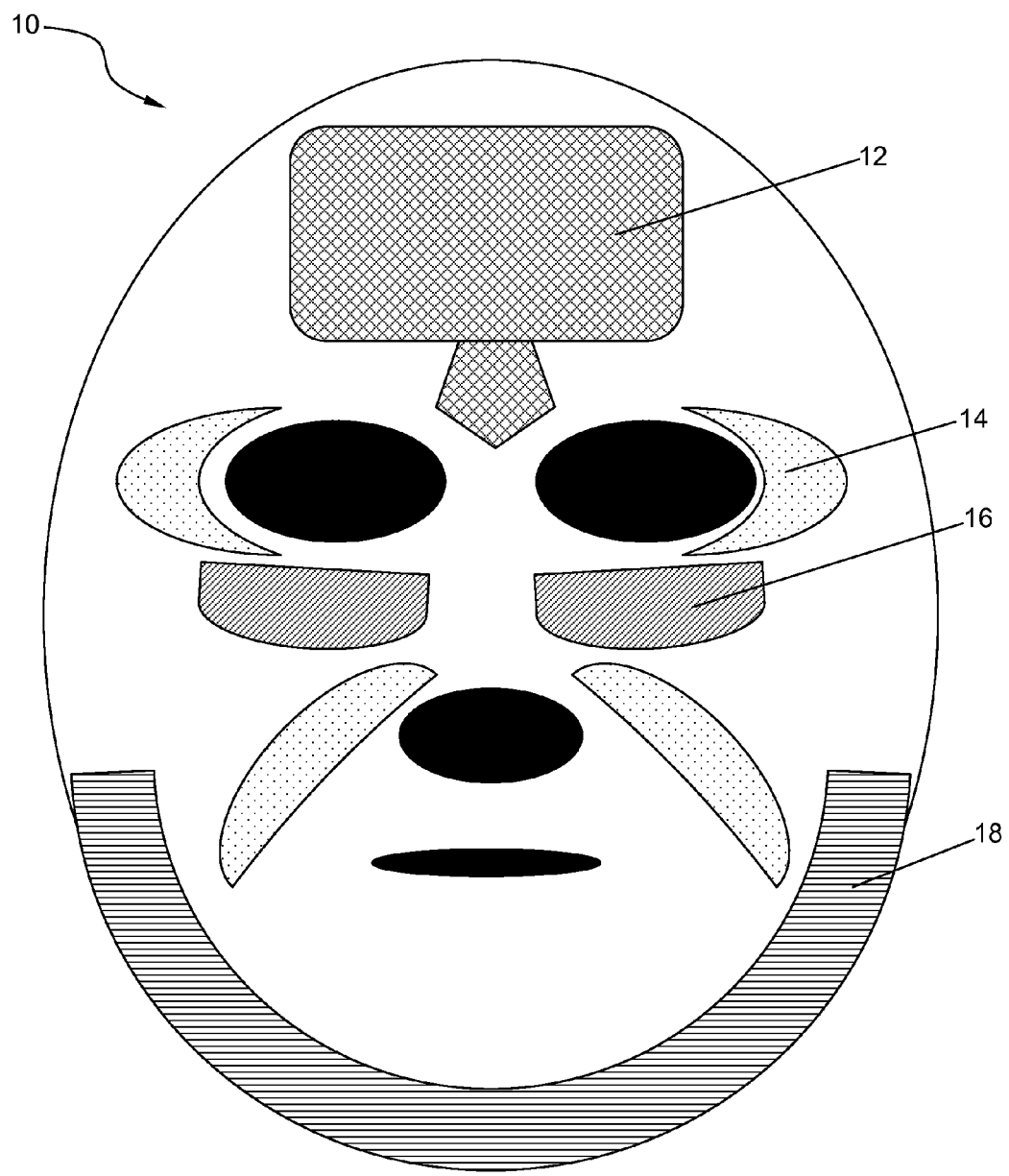
FIG. 1 is a schematic representation of a facial mask containing multiple isolate, discrete regions with different skin benefit agents, according to one embodiment of the present invention.

Reference will now be made in detail to exemplary embodiments of the invention. It is contemplated that a computerized or computer-aided system is used for achieving the targeted and individualized delivery of multiple skin benefit agents to the skin of a user based on the unique skin profile of the user. Cosmetic delivery products produced by the system of the present invention are capable of delivering multiple skin benefit agents to multiple target sections or regions on demand and according to the user skin profile with precise dosage and location control.

Preferably, such a system includes at least an imaging device for capturing an image of the desired treatment area of the user's skin. Such desired treatment skin area may be, for example, full face, partial face, neck, thigh, or the like. In a particularly preferred but not necessary embodiment of the present invention, the desired treatment area is the full face of the user. The imaging device is preferably a digital camera, which may capture the images of the desired treatment area in conjunction with a light source that delivers sufficient and consistent visible or invisible light, such as infrared light or near infrared light. The imaging device can be set in either a manual or an automatic mode for identifying the desired treatment area.

The captured images are directly converted by such imaging device into digital data and stored therein or sent to a personal computer or other computerized analyzing device that is communicatively connected with the imaging device. The analyzing device is programmed for analyzing image data and generating a skin profile indicative of the conditions of the desired treatment area of the user's skin based on the image data. Preferably, the skin profile defines skin regions with certain defects that need certain types of treatment. The term "defects" as used herein broadly covers any types of sub-optimal skin conditions, such as skin dryness, flakiness, redness, oiliness, large pores, dullness, dark spots, uneven skin tone, acne scars, fine lines and wrinkles, under-eye dark circles, under-eye puffiness, cellulite, and the like, or any types of abnormal skin conditions or disorders. More preferably, the skin profile also defines the severity of the skin defects. Such skin profile can be generated using various known algorithms. Examples of these algorithms are described in greater detail by Japanese Patent Application Publication No. 95-231883 entitled "Skin Surface Analysis System and Skin Surface Analysis Method"; International Patent Application Publication No. WO98/37811 entitled "Systems and Methods for the Multispectral Imaging and Characterization of Skin Tissue"; and U.S. Pat. No. 5,016,173 entitled "Apparatus and Method for Monitoring Visually Accessible Surfaces of the Body," the contents of which are incorporated in their entireties for all purposes. Commercially available skin imaging tools that can be used for diagnosing skin defects in the present invention include, for example, the VISIA® Complexion Analysis tools available from Canfield Scientific, Inc. (Fairfield, N.J.), thermal camera system, laser Doppler imaging system, translucency meter, mexameter, Mexameter® MX18 available from CK Electronic (Koln, Germany), the CR series Chroma Meters available from Konica Minolta Business Solutions, U.S.A. (Ramsey, N.J.), the SIAMETRICS™ and COSMETRICS™ skin visualization and measurement systems available from Astron Clinica Ltd. (Cambridge, United Kingdoms), and the like. If the severity of the skin defects is represented by a numerical value, it may be desirable to normalize such value based on the user's ethnic origin, age, geographic location, or any other factor that may have an impact on the user's skin conditions.

Once the skin profile is generated, it is processed by well known photo-editing and illustration software programs, such as Adobe Photoshop Element 4.0, Microsoft PowerPoint 2003, and the like, for creating images to be outputted to a printing device, which corresponding print out one or more cosmetic delivery sheets that are customized for the user based on his or her unique skin conditions. Preferably, the printing device is a printer that contains multiple cartridges, each of which is filled with a composition containing one or more skin benefit agents. Because the conventional thermal inkjet printing mechanism produce high temperature environment at the print head during ink discharging step, which may degrade or destabilize certain skin benefit agents, it is preferred that the printing in the present invention is carried out using a heatless printing mechanism. For example, a pressure-driven ink jet can be used, in which pressure is created on demand by a piezoelectric transducer to change the shape of an internal diaphram in the inkjet print head and therefore force droplets of the skin benefit agents contained in the ink tank to be deposited onto the substrate. Suitable printing devices for the practice of the present invention include, for example, the Epson Workforce series, preferably Epson Workforce 30, the Spectra piezoelectric printers from Fujifilm Dimatix, the RISO HC5500 inkjet printer, and the like. Alternatively, when the skin benefit agents to be delivered are thermally stable or relatively less susceptible to thermal degradation, conventional thermal inkjet printers or low-heat inkjet printers can be used for practice of the present invention.

By using the above-described heatless printing process, the present invention successfully achieves delivery of multiple skin benefit agents with little or no reduction in their biological activities. First, the heatless printing process causes little or no degradation of the skin benefit agents. Second, certain skin benefit agents that are known to interfere with each other's biological activities can be placed into separate cartridges and deposited onto the substrate as separate droplets. More importantly, the droplets of such interfering skin benefit agents are sufficiently small in size that they can be arranged in a scattered manner. Consequently, such skin benefit agents can provide simultaneous treatments to the same region, but without having to be mixed with each other.

The cosmetic delivery sheets so printed could be used anywhere on the face or body skin to predetermined areas for delivery of ingredients via a sheet material mask or patch or similar system. The exact size and shape of the cosmetic sheet will depend upon the intended use and product characteristics. The cosmetic sheets will have sufficient flexibility, and a size and shape adapted to conform to the desired treatment area of the user's skin. In a particularly preferred, but not necessary, embodiment of the present invention, the cosmetic sheet is a facial mask adapted to conform to facial features. It will be understood that a variety of shapes and sizes may be accommodated according to the invention. Such a cosmetic sheet may include a flexible substrate that is formed of, preferably but not necessarily, water-soluble materials, such as sugar or polysaccharides, collagen, and water-soluble film-forming polymers. The substrate contains multiple isolate, discrete regions, while at least two of such regions are imprinted with different skin benefit agents for treating different skin conditions according to the skin profile of the user.

Suitable skin benefit agents can be used in the present invention include, but are not limited to: anti-wrinkle or skin-tightening agents; anti-aging agents; moisturizing agents; skin-whitening or depigmentation agents; anti-inflammatory agents; anti-acne agents; DNA repair agents; skin lipid barrier repair agents; anti-cellulite agents; wound-healing agents; stretch-mark/scar removing agents; plumping agents; hair growth retardation agents; hair growth stimulating agents; dark cycle reduction or de-puffing agents; collagen synthesis or blood circulation enhancing agents; antioxidants; sebum-controlling agents; and pore-minimizing agents. Exemplary anti-wrinkle agents include, but are not limited to, acetyl hexapeptide-8, palmitoyl oligopeptide, dipeptide diaminobutyroyl, benzylamide diacetate, and the like. Exemplary skin-tightening agents include, but are not limited to, algae extract, pullulan, sweet almond seed extract, carbomer, palmitoyl oligopeptide, palmitoyl tetrapeptide-7, *Quercus suber* extract, and the like. Exemplary anti-aging agents include, but are not limited to, teprenone, trisodium resveratrol triphosphate, *Polygonum cuspidatum* root extract, whey protein, and the like. Exemplary moisturizing agents include, but are not limited to, hyaluronic acid, glycerin, urea, trehalose, and the like. Exemplary skin-whitening or depigmentation agents include, but are not limited to, ascorbic acid, magnesium ascorbyl phosphate, aminopropyl ascorbyl phosphate, mulberry root extract, *Scutellaria baicalensis* extract, grape extract, ferulic acid, hinokitol, and the like. Exemplary anti-inflammatory agents include, but are not limited to, spike moss extract, seal whip extract, *Polygonum cuspidatum* root extract, and the like. Exemplary anti-acne agents include, but are not limited to, salicylic acid, glycolic acid, lactobionic acid, and the like. Exemplary DNA repair agents include, but are not limited to, C1-C8 alkyl tetrahydroxycyclohexanoate, micrococcus lysate, bifida ferment lysate, and the like. Exemplary skin lipid barrier repair agents include, but are not limited to, phytosphingosine, linoleic acid, cholesterol, and the like. Exemplary anti-cellulite agents include, but are not limited to, *Coleus forskohlii* root extract, *Magnolia grandiflora* bark extract, *Nelubo nucifera* leaf extract, and the like. Exemplary wound-healing agents include, but are not limited to, *Mimosa tenuiflora* bark extract, soybean protein, and the like. Exemplary plumping agents include, but are not limited to, *Saccharomyces/xylinum* black tea ferment, *Anemarrhena asphodeloides* root extract, sodium hyaluronate, and the like. Exemplary hair growth retardation agents include, but are not limited to, ursolic acid, phytosphingosine, *Boswella serrata* extract, and the like. Exemplary hair growth stimulating agents include, but are not limited to, *Serenoa serrulata* fruit extract, licorice extract, acetyl glucosamine, and the like. Exemplary dark circle reduction or de-puffying agents include, but are not limited to, hesperidin methyl chalcone, dipeptide-2, *Passiflora incarnate* flower extract, linoleic acid, isolinoleic acid, and the like. Exemplary collagen synthesis or blood circulation enhancing agents include, but are not limited to, arginine, *Ascophyllum nodosum* extract, *Asparagopsis armata* extract, caffeine, and the like. Exemplary antioxidants include, but are not limited to, nordihydroguaiaretic acid, grape seed extract, green tea leaf extract, and the like.

The skin benefit agents as described hereinabove can be formulated into an ink formulation that is compatible with the printing device of the present invention. Such ink formulation may be an aqueous solution or an oil-in-water emulsion. When all the skin benefit agents to be delivered are water-soluble, it is preferred that the ink formulation is aqueous. When some of the skin benefit agents are oil-soluble, the ink formulation is preferably a micronized emulsion containing an oil phase in form of micronized oil droplets dispersed in a continuous aqueous phase.

Figure 2:
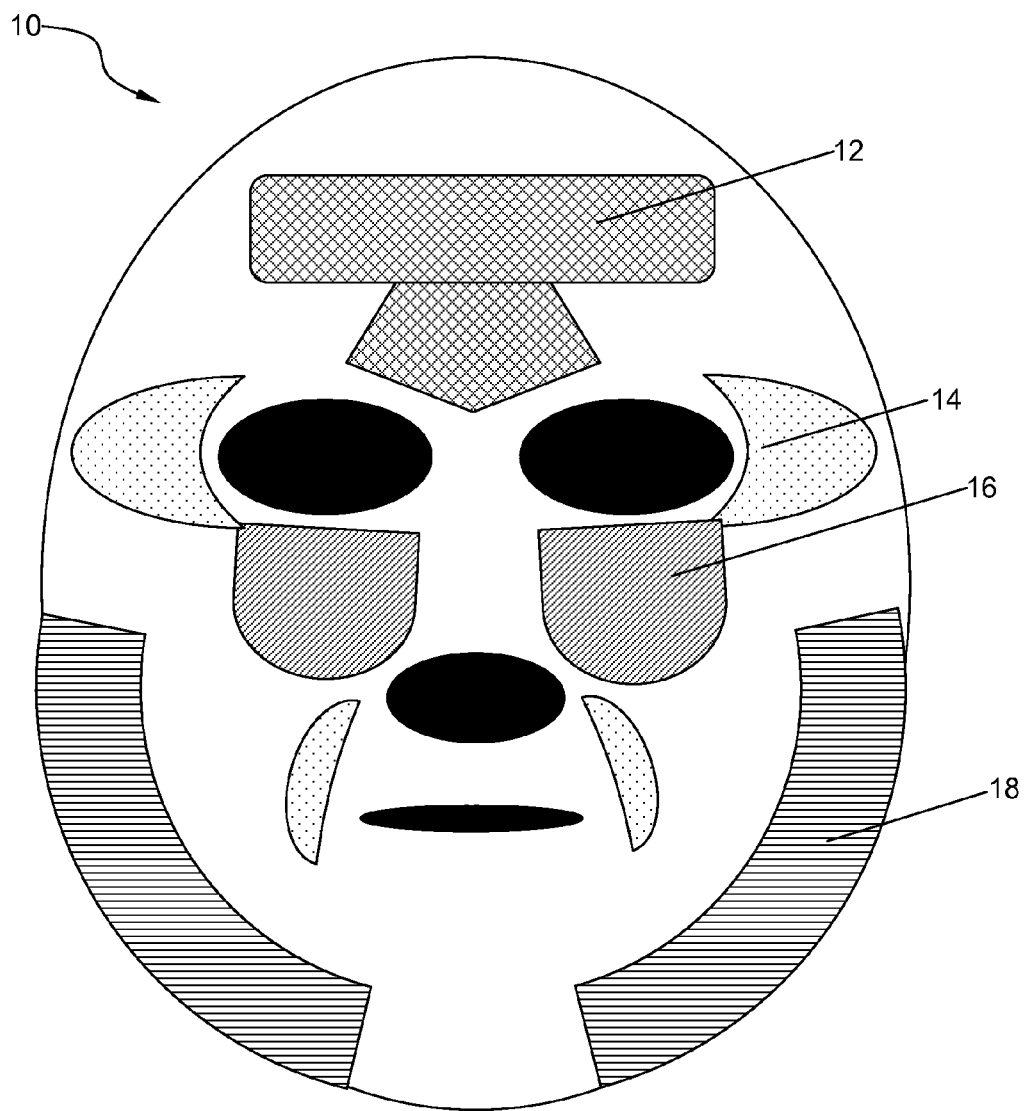
FIG. 2 is a schematic representation of a facial mask according to a second embodiment of the present invention.

FIG. 1 is a schematic view of a facial mask 10 according to one embodiment of the present invention. The facial mask 10 contains multiple discrete regions 12, 14, 16, and 18, which are isolated from one another. Based on the particular skin conditions of the user, regions 12 are imprinted with at least one sebum controlling agent for reducing the oiliness at the T-zone section of the user's face; regions 14 are imprinted with at least one wrinkle reduction or skin-tightening agent for reducing the fine lines and wrinkles at the corners of the user's eyes and mouth; regions 16 are imprinted with at least one dark circle reduction or de-puffying agent; and region 18 is imprinted with at least one anti-cellulite agent. Of course, the discrete regions themselves, may also be customized based on a skin profiling analysis. Customizations include size, shape and number of discrete regions. Preferably, but not necessarily, different regions on the mask 10 may be marked with different colors for easy alignment with different facial features for which the skin benefit agents are intended. FIG. 2 is a schematic representation of a facial mask 10 according to a second embodiment of the present invention.

Figure 3:
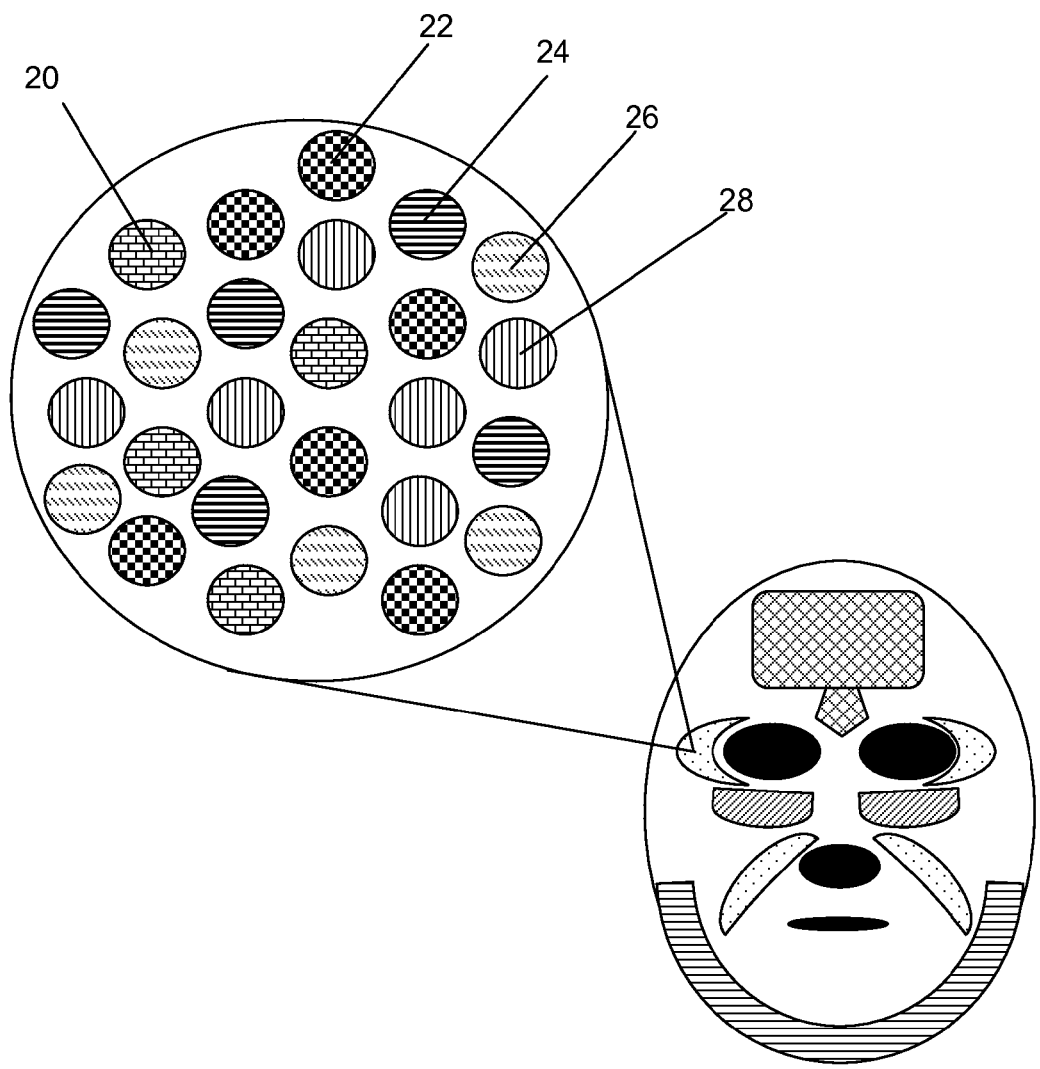
FIG. 3 is an exploded view of one isolate, discrete region on the facial mask of FIG. 1.

FIG. 3 shows an exploded view of the region 14 of FIG. 1. Five different types of skin benefit agents are printed thereon, which include a wrinkle reduction or skin-tightening agent 20, an anti-aging agent 22, an antioxidant agent 24, a moisturizing agent 26, and a plumping agent 28. These skin benefit agents are deposited onto the substrate as separate droplets, which are scattered among one another but without being mixed with one another. In this manner, such skin benefit agents can provide simultaneous treatment to the corners of the user's eyes and mouth with minimum or no interference with one another.

It will be understood by those skilled in the art that, while gel cosmetic sheets suitable for use in the present invention, are naturally tacky, a cosmetic sheet comprised of paper or a textile may require the presence of a cosmetically acceptable adhesive layer associated with the first surface of the support to enhance adherence to the skin. The adhesion of the sheet to the skin may occur via an adhesive compound associated with the surface of the sheet or it may be provided in the form of a gel or liquid, such as water, which moistens the sheet which then clings to skin. The user may also apply the mask to pre-moistened skin. It also is contemplated that a consumer could introduce a liquid activator to the sheet or to specific areas of the sheet which could serve to aid in adhesion of the sheet to the skin, to activate the impregnated formulation, or both. The cosmetic sheet may also be provided with a supporting sheet which can be removed, e.g. peeled away, before the sheet is applied to the skin.

The cosmetic sheet may be formed of any thin, porous, flexible absorbent material, including woven and non-woven fabrics, including felts, paper, natural fibers, synthetic fibers, elastic blends or a mixture thereof. Non-limiting examples include cotton, linen, rayon, thermoplastics, and cellulosics. The sheet material may be a water-soluble material, such as sugar or polysaccharides, collagen, and water-soluble film-forming polymers. The sheet material may also comprise a gel, such as a hydrogel, comprised of, for example, agarose or a water-soluble low-substituted cellulose ether which may include methyl cellulose, hydroxyethyl cellulose, hydroxypropyl cellulose, hydroxypropylmethyl cellulose, hydroxypropylhydroxyethyl cellulose, hydroxyethylmethyl cellulose, ethyl cellulose, hydroxyethylethyl cellulose, or carboxymethyl cellulose. Non-woven fabrics are especially preferred from the viewpoints of cost, productivity and aesthetic feel. Examples of preferred non-woven materials include, but are not limited to, natural and synthetic felts, rice paper or cloth, and bamboo cloth. In a preferred but not necessary embodiment of the present invention, both the substrate and the skin benefit agents of the cosmetic sheet are completely water-soluble, such as sugar or collagen, so upon application of water or like liquid activator, the cosmetic sheet softens and conforms to the skin, and subsequently, the entire sheet is absorbed by the skin surface without having to be removed. Commercially available cosmetic sheets suitable for practice of the present invention include, for example, the sugar-based Frosting Sheets from Kopykake (Torrance, Calif.), the Matricol® Collagen Sheets from Dr. Suwelack Skin & Health Care AG (Billerbeck, Germany), and the 3M™ Transparent 2.6 mil Polyethylene Medical Tape 9830.

Example 1

Targeted Delivery of Caffeine Power

An aqueous solution containing caffeine power was prepared by mixing the following ingredients together:

| Ingredients | wt % |
|---|---|
| Deionized water | QS |
| Butylene glycol | 15.00 |
| Caffeine | 5.00 |
| FD&C Blue No. 1 | 0.04 |
| Phenoxyethanol | 0.50 |
| Total | 100.00 |

The FD&D Blue No. 1 color was provided to mark regions with caffeine power printed thereon. The aqueous solution as described hereinabove was placed into a refillable ink cartridge of an Epson Workforce 30 inkjet printer, which was in turn connected to a personal computer installed with Photoshop Element 4.0. Three different types of substrate sheets, including a sugar-based Frosting Sheet from Kopykake (Torrance, Calif.), a Matricol® Collagen Sheet from Dr. Suwelack Skin & Health Care AG (Billerbeck, Germany), and a 3M™ Transparent 2.6 mil Polyethylene Medical Tape 9830 were fed to the paper tray of the Epson Workforce 30 inkjet printer, and the caffeine-containing aqueous solution was successfully printed onto the substrate sheets by the inkjet printer. The printed substrate sheets were then applied to the skin of a user for targeted delivery of caffeine as a skin benefit agent.

Example 2

Targeted Delivery of Salicylic Acid

An aqueous solution containing salicylic acid was prepared by mixing the following ingredients together:

| Ingredients | wt % |
|---|---|
| Deionized water | QS |
| Isopentyldiol | 40.00 |
| Salicylic acid | 1.00 |
| FD&C Yellow No. 5 | 0.04 |
| Phenoxyethanol | 0.50 |
| Total | 100.00 |

The FD&D Yellow No. 5 color was provided to mark regions with salicylic acid (SA) printed thereon. The aqueous solution as described hereinabove was placed into a refillable ink cartridge of an Epson Workforce 30 inkjet printer, which was in turn connected to a personal computer installed with Photoshop Element 4.0. Three different types of substrate sheets, including a sugar-based Frosting Sheet from Kopykake (Torrance, Calif.), a Matricol® Collagen Sheet from Dr. Suwelack Skin & Health Care AG (Billerbeck, Germany), and a 3M™ Transparent 2.6 mil Polyethylene Medical Tape 9830 were fed to the paper tray of the Epson Workforce 30 inkjet printer, and the SA-containing aqueous solution was successfully printed onto the substrate sheets by the inkjet printer. The printed substrate sheets were then applied to the skin of a user for targeted delivery of SA as a skin benefit agent.

Although the present invention has been described in accordance with preferred embodiments, it will be understood by those skilled in the art that various changes and modifications may be made without departing from the spirit and scope of the invention.

What is claimed is:

1. A system for targeted and individualized delivery of multiple skin benefit agents to the skin of a user comprising:

an imaging device for capturing an image of a predetermined treatment area of the user's skin;

an analyzing device communicatively connected with said imaging device for receiving data representative of the captured image from the imaging device, analyzing such data, and generating a skin profile indicative of the conditions of the predetermined treatment area of the user's skin; and a printing device communicatively connected with said analyzing device for printing one or more cosmetic delivery sheets, wherein said cosmetic delivery sheets are arranged and constructed for conforming to the predetermined treatment area of the user's skin, wherein each of said cosmetic delivery sheets comprises a substrate with multiple isolate, discrete regions, wherein at least two of the isolate, discrete regions are imprinted with different skin benefit agents for treating different skin conditions of the predetermined treatment area according to the skin profile generated by the analyzing device.

2. The system of claim 1, wherein the imaging device is a digital camera.

3. The system of claim 1, wherein the analyzing device is a personal computer programmed to process the captured image data and generate the skin profile.

4. The system of claim 1, wherein the printing device is a printer equipped with cartridges that are filled with compositions containing skin benefit agents, and wherein the printing device is constructed to print the compositions containing the skin benefit agents onto the substrate of the cosmetic delivery sheet through a heatless printing process.

5. The system of claim 4, wherein both the substrate and the skin benefit agents are water-soluble, so that the cosmetic delivery sheets so formed can be completely absorbed by the skin of the user after application thereon.

6. A method for targeted and individualized delivery of multiple skin benefit agents to the skin of a user comprising:

capturing an image of a predetermined treatment area of the user's skin;

analyzing the captured image data;

generating a skin profile indicative of the conditions of the predetermined treatment area of the user's skin; and printing one or more cosmetic delivery sheets based on the generated skin profile, wherein said cosmetic delivery sheets are arranged and constructed for conforming to the predetermined treatment area of the user's skin, wherein each of said cosmetic delivery sheets comprises a substrate with multiple isolate, discrete regions, wherein at least two of the isolate, discrete regions are imprinted with different skin benefit agents for treating different skin conditions of the predetermined treatment area.

* * * * *